United States Patent [19]

Hardt

[11] Patent Number: 4,607,720

[45] Date of Patent: Aug. 26, 1986

[54] HEARING AID

[75] Inventor: Heinz Hardt, Vienna, Austria

[73] Assignee: Viennatone Gesellschaft m.b.H., Vienna, Austria

[21] Appl. No.: 760,154

[22] Filed: Jul. 29, 1985

[30] Foreign Application Priority Data

Aug. 6, 1984 [AT] Austria ................................ 2547/84

[51] Int. Cl.4 ................................................ A61B 7/02

[52] U.S. Cl. ................................ 181/135; 179/107 E

[58] Field of Search ................................ 181/130–135; 179/107 E, 107 S, 107 H

[56] References Cited

U.S. PATENT DOCUMENTS

| | | | |
|---|---|---|---|
| 2,266,788 | 12/1941 | Nelson et al. | 181/132 X |
| 3,209,082 | 9/1965 | McCarrell et al. | 179/107 E |
| 3,882,848 | 5/1975 | Klar et al. | 181/135 X |
| 4,055,233 | 10/1977 | Huntress | 181/135 |
| 4,314,553 | 2/1982 | Westerdal | 179/107 E X |
| 4,375,016 | 2/1983 | Harada | 181/135 X |
| 4,532,649 | 7/1985 | Bellafiore | 179/107 E X |

*Primary Examiner*—Benjamin R. Fuller
*Attorney, Agent, or Firm*—Kurt Kelman

[57] ABSTRACT

To provide a mass-producing hearing aid adapted to be inserted into the external passage of the vast majority of human ears while leaving the concha unencumbered and without requiring individual impressions, the invention proposes a hearing aid which comprises a housing, a coupling element connected to the housing in communication with the sound emission opening of the hearing aid, and a sealing plug detachably connected to the coupling element and having an end remote from the housing, the sealing plug being comprised of cylindrical inner part mounted on the coupling element and an outer part turned back from the inner part at the remote end.

10 Claims, 5 Drawing Figures

HEARING AID

The present invention relates to a hearing aid having a sound emission opening and adapted to be substantially fully inserted into the external passage of an ear and which comprises a housing carrying such hearing aid components as an amplifier, an earphone, a microphone and a battery.

Hearing aids have become progressively smaller during the last few years and thus come closer to the desire of the hard-of-hearing for obtaining an invisible prosthesis. By using the latest technology, hearing aids have recently been built small enough to fit into the external passage of the ear. However, a necessary condition for this was that the hearing aid had to be built into a "trough" individually prepared from an impression of the patient's ear. This alone assured a secure seating of the hearing aid and the good seal required for acoustic reasons. Practically each such hearing aid, therefore, had a different shape and had to be prepared individually for each patient, which is very time-consuming and accordingly expensive.

It is the primary object of this invention to provide a hearing aid adapted to be substantially fully inserted into the external passage of an ear but which may be mass-produced while affording a simple and economically attainable, effective sealing of the external ear passage accurately adaptable to each user.

The above and other objects are accomplished in a hearing aid of the above-indicated type with a coupling element connected to the housing in communication with the sound emission opening, and a sealing plug detachably connected to the coupling element and having an end remote from the housing, the sealing plug being comprised of cylindrical inner part mounted on the coupling element and an outer part turned back from the inner part at the remote end.

Tests on a great number of human ears have proved that a standard shape may readily be established for fitting the vast majority of all ears and that, therefore, the hearing aid of the invention may be mass-produced. These mass-produced hearing aids may readily be adapted for insertion into individual ears by providing detachable sealing plugs of selected sizes and by mounting a fitting plug of the selected size on the coupling element. The sealing,plug of the present invention provides a secure seat for the hearing aid housing, its inner part being securely mounted on the coupling element, as well as an exact sealing of the external ear passage with the outer part to obtain the optimum acoustic conditions.

Figure 1C:
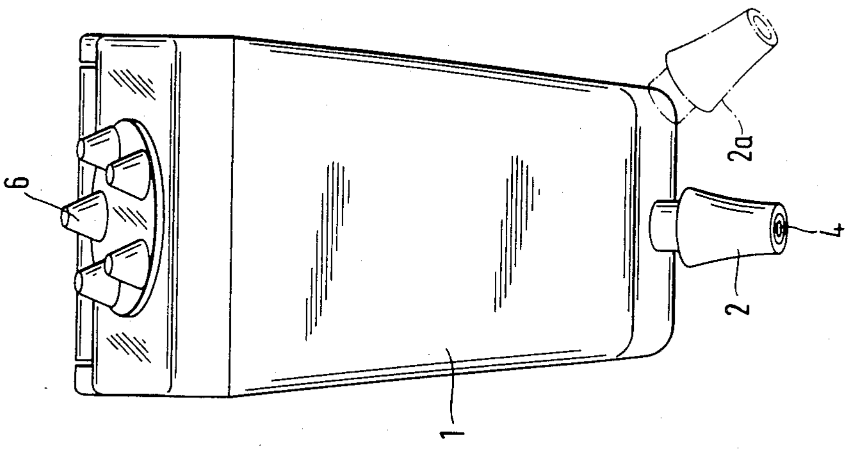
Figure 1:
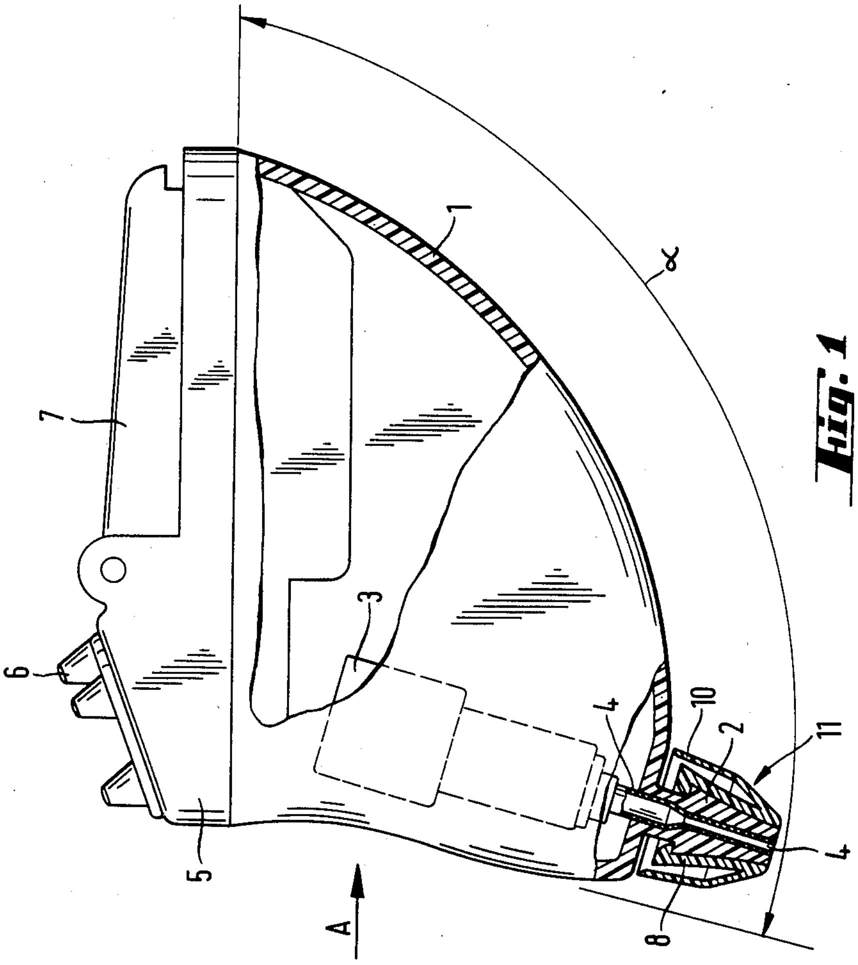
Figure 1B:
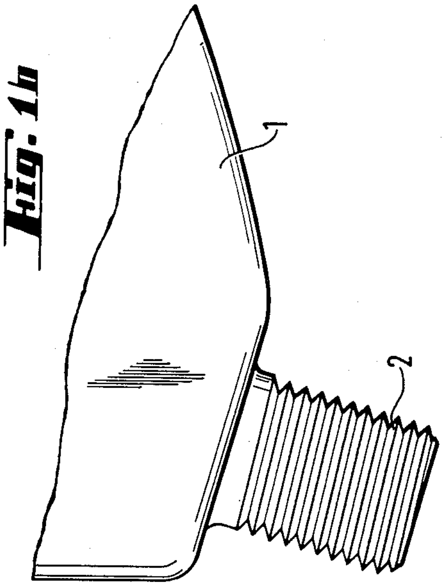
Figure 1A:
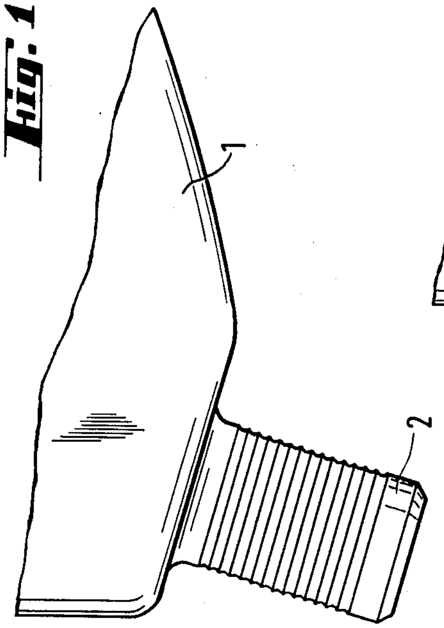

The above and other objects, advantages and features of this invention will become more apparent from the following detailed description of now preferred embodiments thereof, taken in conjunction with the accompanying drawing wherein FIG. 1 is a side elevational view of a hearing aid according to the invention, partly in section;

FIGS. 1*a* and 1*b* are enlarged fractional side views showing two embodiments of the coupling element in detail;

FIG. 1*c* is a perspective end view of the hearing aid; and

Figure 2:
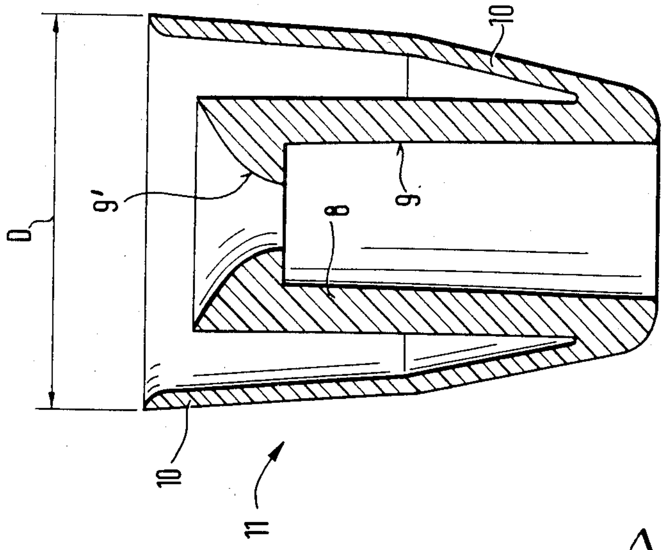

FIG. 2 is an enlarged cross section of the detachable sealing plug.

Referring now to the drawing, the hearing aid is shown to comprise housing 1 which receives the hearing aid components. It is made of synthetic resin or metal and has as thin a wall as possible. Coupling element 2 is connected to housing 1 in communication with the sound emission opening of earphone or sound receiver 3 built into housing 1 at a lower end of the housing. The connection of the coupling element to the housing may be effected by soldering, rivetting, bonding or any other suitable connecting means. The coupling element may also be integral with the housing, as shown. The sound emission opening is connected with coupling element 2 by hose 4 passing through an axial bore in the coupling element. Any other suitable connection will readily occur to those skilled in the art. Since this is well known, such other built-in hearing aid components as microphone, amplifier, etc. have not been shown in the drawing.

As shown in FIG. 1*c*, the hearing aid has a center axis and coupling element 2 is coaxial with the center axis whereby the structure is fully symmetrical. However, as shown in broken lines, a symmetrical hearing aid may also be provided by pivoting the connecting element from the center axis into a position to the right or to the left of the center axis, thus improving its fit and increasing the wearing comfort of the hearing aid as a "right" or "left" hearing aid.

Furthermore, as illustrated in FIG. 1, to enable the hearing aid to fit as many ears as possible, experiments have shown that the preferred shape of housing 1 is that of a sector of a circle delimited by two radial lines enclosing an angle of about 85° to 110°, in a section extending parallel to the large surface of the housing. As usual, the top of the housing is closed by cover plate 5 which carries sound level adjustment plate 6 and battery cover 7.

According to the invention, mushroom-shaped sealing plug 11 is detachably connected to coupling element 2. The sealing plug is comprised of cylindrical inner part or sleeve 8 mounted the coupling element and outer part 10 turned back from the inner part at an end of the sealing plug remote from housing 1. The outer sealing plug part has a thinner wall than wall 9 of the inner part. In this way, the thick inner part wall provides sufficient stability and a solid connection to coupling element 2 while the thin outer sealing plug wall assures ready adaptation to the wall of the external ear passage to provide a good seal. This ready deformability is enhanced if the sealing plug is comprised of a material having an A-Shore hardness not exceeding 70° and is selected from the group consisting of soft polyvinylchloride and rubber, preferably silicone rubber.

Different sizes of the detachable sealing plug enabling the hearing aid to fit various external ear passages are essentially differentiated from each other only by a difference in their outer diameter D (see FIG. 2). To enable the sealing plug to be readily replaced on the connecting element, a suitably simple and quick-release connection is desirable. For example, a snap connection may be provided for mounting inner sealing plug part 9 on coupling element 2, as shown in FIG. 1. In the illustrated snap connection, the connecting element is frusto-conical to form an annular shoulder and inner sealing plug part wall 9 has inwardly directed annular flange 9' snapping over and engaging the shoulder of the frustoconical connecting element.

FIG. 1*a* shows another firm, yet readily detachable connection between the sealing plug and the connecting element for mounting the plug on the coupling element. In this case, connecting element 2 is cylindrical and has a series of alternating circumferential grooves and ribs to provide a frictional connection. FIG. 1*b* illustrates a threaded connection for mounting the sealing plug on the coupling element. Bayonet and other types of connections may also be used.

What is claimed is:

1. A hearing aid having a sound emission opening and adapted to be substantially fully inserted into the external passage of an ear, which comprises (a) a housing containing a sound receiver, (b) a coupling element connected to the housing in communication with the sound emission opening, and (c) a sealing plug detachably connected to the coupling element and having one end adjacent the housing and another end remote from the housing, the sealing plug being comprised of (1) a cylindrical inner part mounted on the coupling element and (2) a substantially cylindrical outer part surrounding the inner part and turned back from the inner part at the remote end and extending to the one end of the sealing plug, the inner and outer parts defining an annular gap therebetween extending to the one end of the sealing plug adjacent the housing.

2. The hearing aid of claim 1, further comprising a snap connection for mounting the inner sealing plug part on the coupling element.

3. The hearing aid of claim 1, further comprising a frictional connection between the coupling element and the sealing plug for mounting the plug on the coupling element.

4. The hearing aid of claim 1, further comprising a threaded connection for mounting the sealing plug on the coupling element.

5. The hearing aid of claim 1, wherein the outer sealing plug part has a thinner wall than the inner part.

6. The hearing aid of claim 1, wherein the sealing plug is comprised of a material having an A-Shore hardness not exceeding 70° and is selected from the group consisting of soft polyvinylchloride and rubber.

7. The hearing aid of claim 6, wherein the rubber is silicone rubber.

8. The hearing aid of claim 1 and having a center axis, wherein the coupling element is coaxial with the center axis.

9. The hearing aid of claim 1 and having a center axis, wherein the coupling element is pivoted from the center axis into a position to the right or to the left of the center axis.

10. The hearing aid of claim 1, wherein the housing has the shape of a sector of a circle delimited by two radial lines enclosing an angle of about 85° to 110°.

* * * * *